US011197982B2

(12) United States Patent
Heister

(10) Patent No.: US 11,197,982 B2
(45) Date of Patent: Dec. 14, 2021

(54) ENDOVASCULAR BALLOON CATHETER

(71) Applicant: David Sharpe Heister, Little Rock, AR (US)

(72) Inventor: David Sharpe Heister, Little Rock, AR (US)

(*) Notice: Subject to any disclaimer, the term of this patent is extended or adjusted under 35 U.S.C. 154(b) by 326 days.

(21) Appl. No.: 16/361,630

(22) Filed: Mar. 22, 2019

(65) Prior Publication Data

US 2020/0297979 A1 Sep. 24, 2020

(51) Int. Cl.
*A61M 25/10* (2013.01)
*A61M 25/00* (2006.01)
*A61B 17/00* (2006.01)

(52) U.S. Cl.
CPC .... *A61M 25/1002* (2013.01); *A61M 25/0068* (2013.01); *A61B 2017/00243* (2013.01); *A61M 25/1018* (2013.01); *A61M 2025/109* (2013.01); *A61M 2025/1093* (2013.01)

(58) Field of Classification Search
CPC .......... A61M 25/1002; A61M 25/0068; A61M 2025/109; A61M 2025/1093; A61M 25/1018; A61M 25/04; A61M 2025/1084; A61M 2025/1075; A61M 2025/0233; A61B 2017/00243; A61B 17/22032; A61B 2017/22094; A61B 2017/22069; A61B 2017/11
See application file for complete search history.

(56) References Cited

U.S. PATENT DOCUMENTS

| | | | |
|---|---|---|---|
| 5,795,325 A * | 8/1998 | Valley | A61B 17/12022 604/509 |
| 2003/0104073 A1 | 6/2003 | Johansson et al. | |
| 2007/0060882 A1 | 3/2007 | Tal | |
| 2011/0245665 A1 | 10/2011 | Nentwick | |
| 2015/0032142 A1* | 1/2015 | Silvestro | A61M 25/0194 606/185 |
| 2015/0051632 A1* | 2/2015 | Sina | A61M 29/02 606/194 |

OTHER PUBLICATIONS

Definition of Adjacent, https://www.oed.com/view/Entry/2414?redirectedFrom=adjacent#eid (Year: 2021).*
Definition of Compliant, https://www.oed.com/view/Entry/37700?redirectedFrom=compliant& (Year: 2021).*
International Search Report and Written Opinion dated Jun. 16, 2020 for PCT Patent Application No. PCT/US20/23822.

* cited by examiner

*Primary Examiner* — Theodore J Stigell
*Assistant Examiner* — Rachel T. Smith
(74) *Attorney, Agent, or Firm* — William A. English; Vista IP Law Group LLP

(57) ABSTRACT

A balloon catheter is disclosed for endovascular procedures. In one embodiment, among others, the balloon catheter includes an elongated catheter body. At a distal end, the catheter body also includes an angled tip and a balloon adjacent to the angled tip. The balloon is inflatable to form an oblong shape.

18 Claims, 8 Drawing Sheets

ENDOVASCULAR BALLOON CATHETER

BACKGROUND

Hemodialysis is a common procedure that patients undergo when experiencing kidney failure. Preserving vascular access is a high priority for these patients as adequate vascular access is required for hemodialysis procedures. The use of surgically created arteriovenous fistulas and arteriovenous grafts have been advocated as a first option in hemodialysis patients. Arteriovenous fistulas and arteriovenous grafts are high velocity connections that are created between an artery and a vein and are ideal for adequate hemodialysis.

BRIEF DESCRIPTION OF THE DRAWINGS

Many aspects of the present disclosure can be better understood with reference to the following drawings. The components in the drawings are not necessarily to scale, with emphasis instead being placed upon clearly illustrating the principles of the disclosure. Moreover, in the drawings, like reference numerals designate corresponding parts throughout the several views.

DETAILED DESCRIPTION

Figure 1:
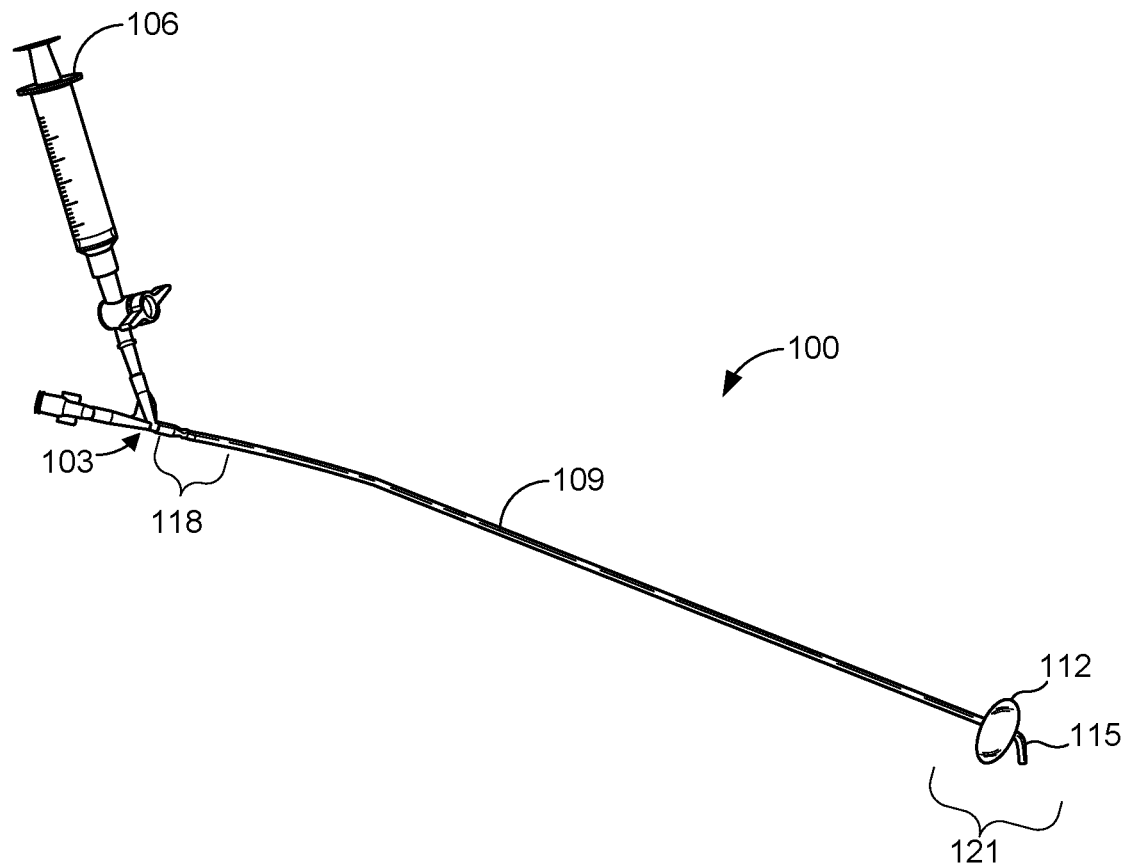
FIG. 1 is a perspective view of an exemplary balloon catheter, according to one embodiment described herein.

The present application relates to an endovascular balloon catheter that enables changing the direction of an angled tip of the balloon catheter within a lumen, such as a blood vessel. In many cases, endovascular procedures need multiple vascular access points in a patient in order to accomplish a procedural objective. For example, hemodialysis is a common medical procedure in which preserving vascular access is a high priority in order to continue performing hemodialysis procedures in the future. The use of surgically created arteriovenous fistulas (AVFs) and arteriovenous grafts (AVGs) has been advocated as the first option in hemodialysis patients. AVFs and AVGs are high velocity connections that are created between an artery and a vein and are ideal for adequate hemodialysis.

However, these vascular accesses have limited durability with a tendency to narrow and ultimately occlude (e.g., thrombose) over time. In some cases, it is estimated that AVG thrombosis occurs approximately 0.5-2.0 times per year and AVF thrombosis occurs 0.1-0.5 times a year. It is also believed that thrombosis accounts for approximately 65-85% AVF/AVG loss. To minimize the loss of AVFs and AVGs, several techniques have been developed to reopen (e.g., declot) these vascular circuits. Illustrative examples of such techniques include the use of thrombin dissolving medicine (e.g., tissue plasminogen activator), mechanical thrombectomy, and/or balloon thrombectomy.

Despite the different methods for clot removal, all of these methods typically require obtaining two separate non-overlapping vascular access sites within a blood vessel directed in opposite directions. For instance, there is a first vascular access site in a blood vessel for accessing an anterograde direction (venous outflow) and a second vascular access site for accessing a retrograde direction (arterial inflow). The operator can only treat the blood vessel in front of the vascular access site. During a traditional declot procedure, thrombolysis and thrombectomy are first performed from the outflow sheath to clear a thrombus (e.g., blockages) from the venous outflow using a first vascular access site. Once the venous side of the access is cleared, thrombolysis and thrombectomy is then performed from the inflow or retrograde sheath directed toward the arterial inflow using a second vascular access site. Once both the inflow and outflow are cleared of the thrombus, attention is then turned to identify and treat residual stenoses, before sheaths are removed and hemostasis is obtained at both access sites.

Existing catheters can only push or pull a clot out in the direction of its original access and as a result, two access sites are needed in order to access both directions. When two access sites are involved, additional surgical equipment may be needed to perform a declot procedure (e.g., two sheaths, angled catheter, a straight thrombectomy balloon).

The various embodiments of the present disclosure relate to an improved endovascular catheter with an angled tip and an inflatable oblong-shaped balloon. The embodiments of the present disclosure enable for endovascular thrombectomy procedures to be performed more safely due to the need for a single access site, more efficiently, and with less surgical equipment. For example, the embodiments can reduce the need for one-third of the steps typically performed during a declot procedure because the embodiments can reorient the balloon catheter in both an anterograde direction and a retrograde direction from a single vascular access site.

With reference to FIG. 1, shown is a perspective view of a balloon catheter 100 connected to a catheter hub 103, in which the catheter hub 103 is connected to a syringe 106. The balloon catheter 100 comprises a catheter body 109, a balloon 112, and angled tip 115.

Figure 4A:
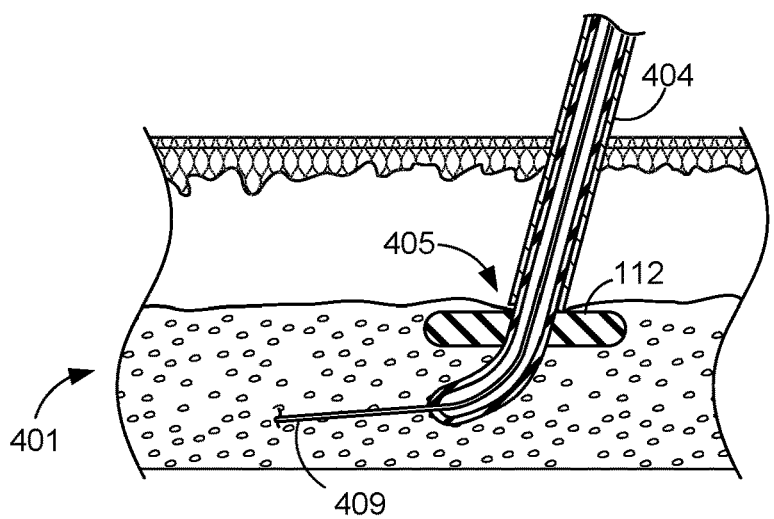
FIG. 4A is a view of the balloon catheter from FIG. 1 within a blood vessel, according to one embodiment described herein.
Figure 4B:
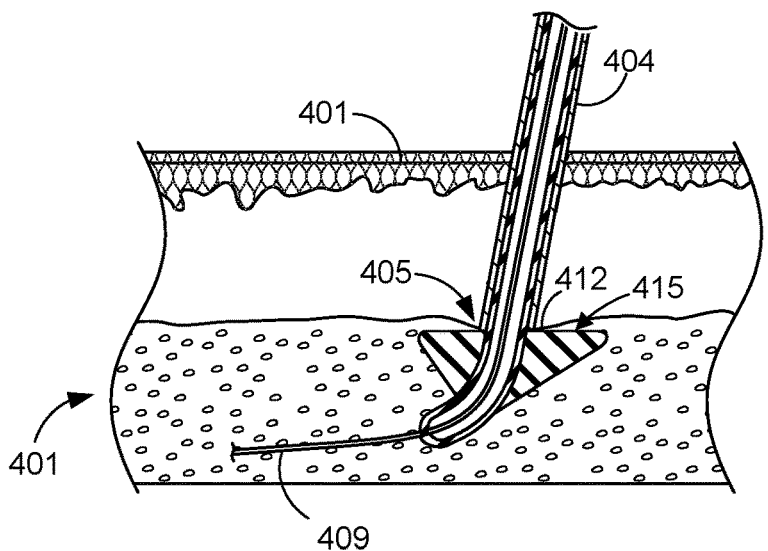
FIG. 4B is a view of a balloon catheter with a first alternative balloon shape, according to one embodiment described herein.
Figure 4C:
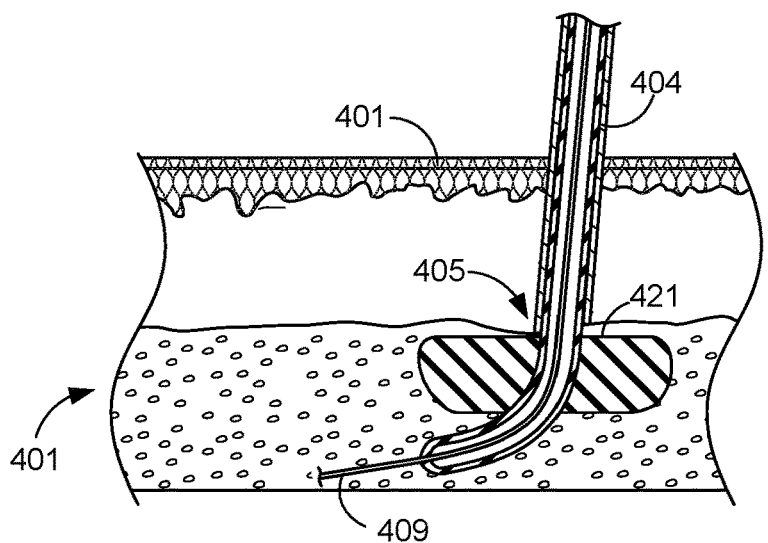
FIG. 4C is a view of a balloon catheter with a second alternative balloon shape, according to one embodiment described herein.

The catheter body 109 has an elongated cylindrical shape between a first end 118 and a second end 121. The catheter body 109 can be connected to the catheter hub 103 on the first end 118. At the second end 121, the catheter body 109 can include the balloon 112 adjacent to the angled tip 115. The catheter hub 103 can comprise a first port that connects to the catheter body 109 at the first end 118. The catheter hub 103 can also comprise a second port that connects to the syringe 106 and a third port for inserting a guide wire (FIGS. 4A, 4B, and 4C).

The catheter body 109 can have a diameter in a range between 1.25 mm and 2.25 mm. In some embodiments, the catheter body 109 has a diameter of 1.667 mm (e.g., 5 French). The balloon 112 can be used to push, pull, and/or remove blockages within a lumen. As one skilled in the art can appreciate, the balloon 112 can be used for other endovascular actions. The balloon 112 can comprise a compliant balloon, a non-compliant balloon, and other suitable balloon materials. When inflated, the balloon 112 can be configured to form an oblong shape, where a length of the balloon 112 is longer than its width. In some non-limiting examples, an oblong shape may comprise a donut shape, an oval, a rectangle, and other suitable oblong shapes. When deflated, an outer surface of the balloon 112 can be in alignment with an outer surface of the catheter body 109.

When inflated, the shape of the balloon 112 can used to anchor the balloon 112 against an inner surface of a blood vessel wall surrounding a vessel access point. Particularly, the shape and dimensions of the balloon 112 provide sufficient surface area such that the balloon 112 can be used as an anchor to rotate the angled tip 115 within a vessel. When the balloon 112 is positioned adjacent to the vessel access point, the surface area of the balloon 112 prevents that balloon from moving out of the vessel access point.

Figure 2A:
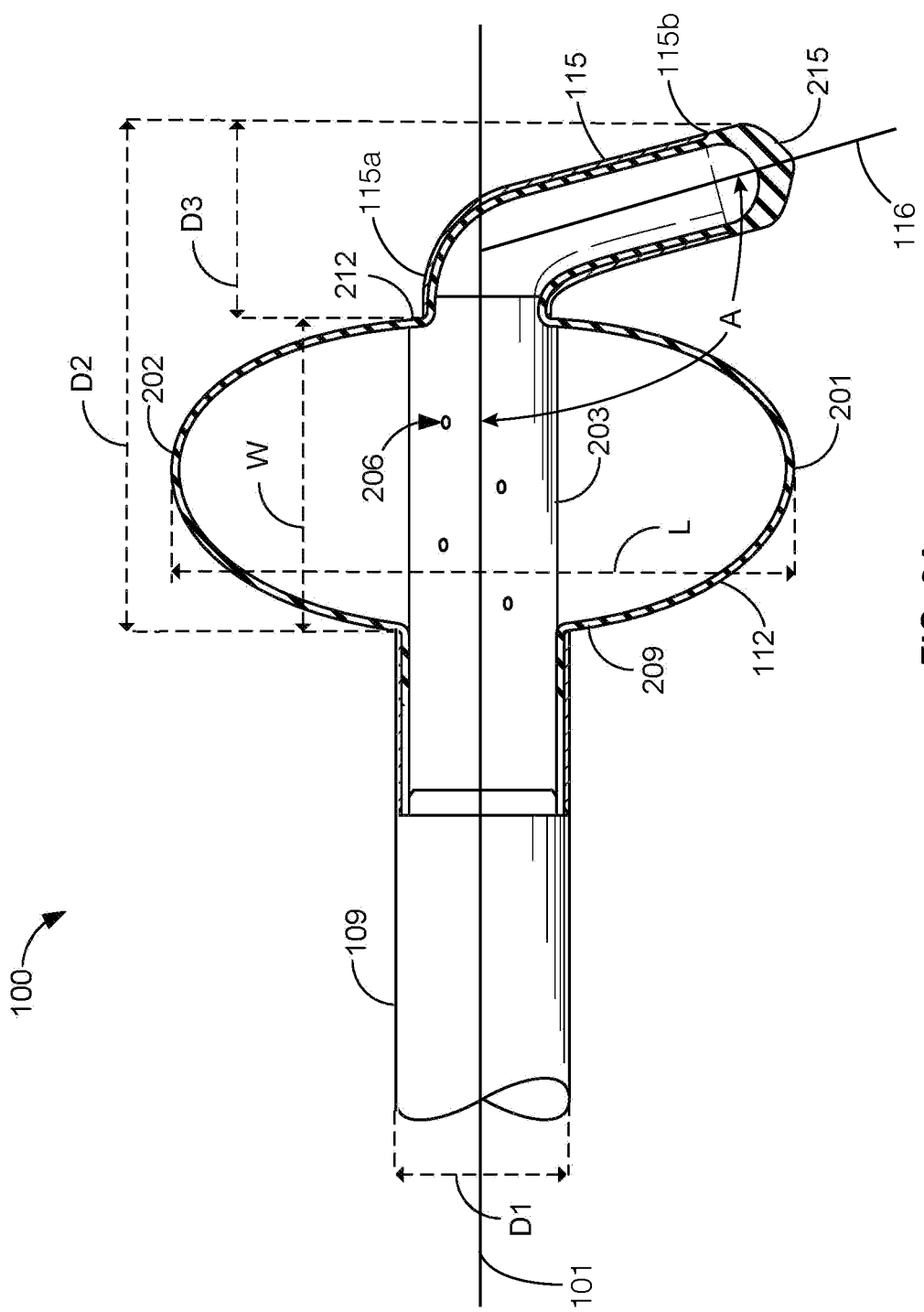
FIG. 2A is a first cross-sectional view of the balloon catheter from FIG. 1 in which the balloon is in an inflated state and a portion of an outer surface of the catheter body is omitted, according to one embodiment described herein.

The balloon catheter 100 also comprises an angled tip 115 that can be adjacent to the balloon 112, e.g., integrally formed with and extending from the bottom surface 212 of the balloon 112 and including a substantially straight portion 115b extending from a curved region 115a parallel to a tip axis 116 of the angled tip 115, as shown in FIG. 2A. In some embodiments, the curve of the angled tip 115 can begin adjacent to a distal end of the balloon 112, e.g., immediately adjacent the bottom surface 212, as also shown in FIG. 2A. In other embodiments, portions of the balloon 112 can extend along areas of the angled tip 115. In this non-limiting example, during an inflated state, portions of the balloon 112 may surround a portion of the angled tip 115. The arrangement of the balloon 112 and the angled tip 115 provide a means for the end of the angled tip 115 of the balloon catheter 100 to be rotated from a first direction to a second direction within a lumen while the balloon 112 is inflated. The balloon 112 may be inflated with a gas (e.g., air), a liquid, or by other suitable means as can be appreciated by one skilled in the art.

With reference to FIG. 2A, shown is a first cross-sectional view of the balloon 112 and angled tip 115 from FIG. 1, particularly with the balloon 112 inflated between a first balloon end 201 and a second balloon end 202. As shown in FIG. 2A, the catheter body 109 comprises an inner tube 203 with multiple openings 206. A gas or liquid from the syringe 106 (FIG. 1) can travel through the openings 206 to inflate the balloon 112. The number of openings 206, the shape of the openings 206, and the opening locations can vary.

As previously discussed, the catheter body 109 may have a diameter, referenced by "D1" in FIG. 2A. In some embodiments, the diameter D1 may be in a range between 1.25 mm and 2.25 mm. When inflated, the balloon 112 comprises a top surface 209 and a bottom surface 212. The balloon 112 may also have a length, referenced by "L," in a range between 0.25 mm and 7.0 mm. In some examples, the length "L" of the balloon 112 in an inflated state is about 6 mm. In some non-limiting examples, the length "L" of the balloon 112 and the diameter "D1" of the catheter body 109 may have a ratio(D1/L) of in a range about 0.20 to 0.3. In some examples, the ratio is about 0.2666. Additionally, the balloon 112 may have a width, referenced by "W," in a range between 0.25 mm and 6.25 mm in an inflated state. In some non-limiting examples, the width "W" is about 2 mm. The distance, referenced by "D2," from the top surface 209 of the balloon 112 to an end 215 of the angled tip 115 can be less than 6.5 mmm, and in some examples, the distance "D2" may be in a range between 4.5 mm to 5.5 mm. In other examples, the distance "D2" may be in a range between 0.25 to 6.5 mm. Further, a distance, referenced by "D3," from the bottom surface 212 of the balloon 112 to the end 215 of the angled tip 115 may be in a range between 1.5 mm and 3.5 mm. In some examples, the distance "D3" may be about 2.5 mm.

Further, the angled tip 115 may be configured at an angle between a longitudinal axis 101 of the catheter body 109 and the tip axis 116, referenced by "A" in FIG. 2A, between the catheter body 109 and an extend member of the angled tip 115. The angle "A" can vary in a range from 125 degrees to 175 degrees. In some examples, the angle "A" is about 150 degrees. In some non-limiting examples, as illustrated in FIG. 2A, the end 215 of the angled tip 115 does not extend pass the first balloon end 201 of the balloon 112 in its inflated state. In some embodiments, the end 215 of the angled tip 115 is alignment with the first balloon end 201

Figure 2B:
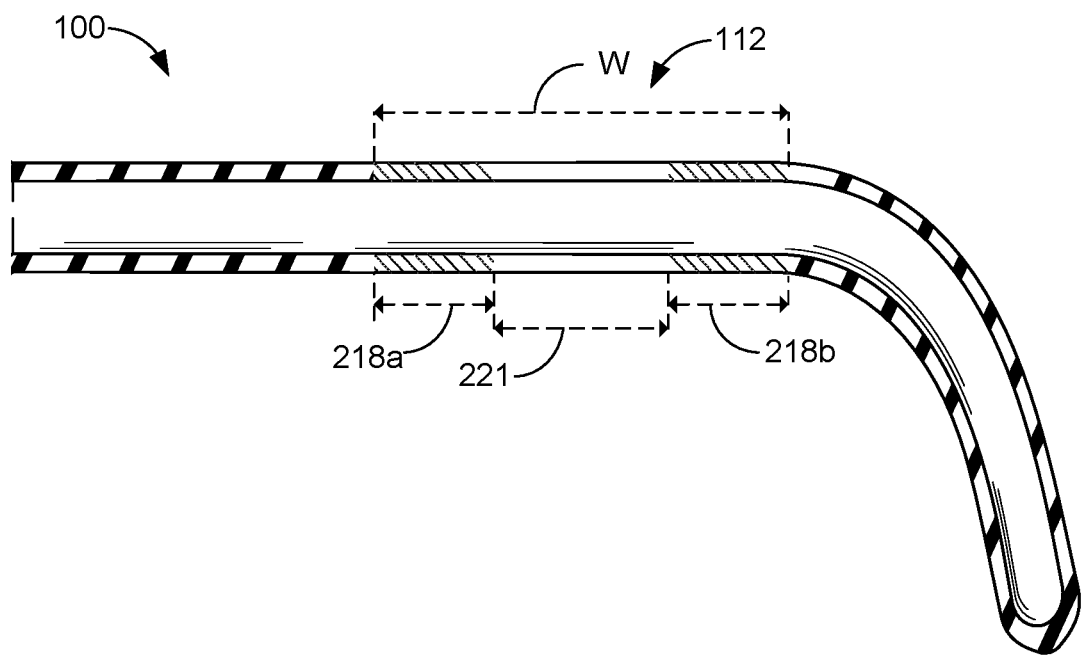
FIG. 2B is a second cross-sectional view of the balloon catheter from FIG. 1 in which the balloon is in a deflated state, according to one embodiment described herein.

Moving to FIG. 2B, shown is a cross-sectional view of the second end 121 of the balloon catheter 100, particularly a cross-sectional view of the balloon 112 and the angled tip 115 when the balloon 112 is in a deflated state. In FIG. 2B, the balloon channels (FIG. 2C) are omitted. In some embodiments, along the width "W" of the balloon 112, the composition of the balloon materials may vary. For example, the outer regions 218 a,b along the width "W" of the balloon 112 may be comprised of balloon materials that are less elastic than a center region 221 of the width "W" of the balloon 112. In another non-limiting example, the outer regions 218a,b may be comprised of non-compliant balloon materials, and the center region 221 may be comprised of compliant balloon materials. In this non-limiting example, the outer regions 218 a,b can expand or stretch to predefined dimensions. Since the center region 221 is comprised of compliant balloon materials, it can expand further than the predefined dimensions. The different compositions of balloon materials along the width "W" can facilitate the balloon 112 conforming to an elongated length "L" that is longer than the width "W."

Figure 2C:
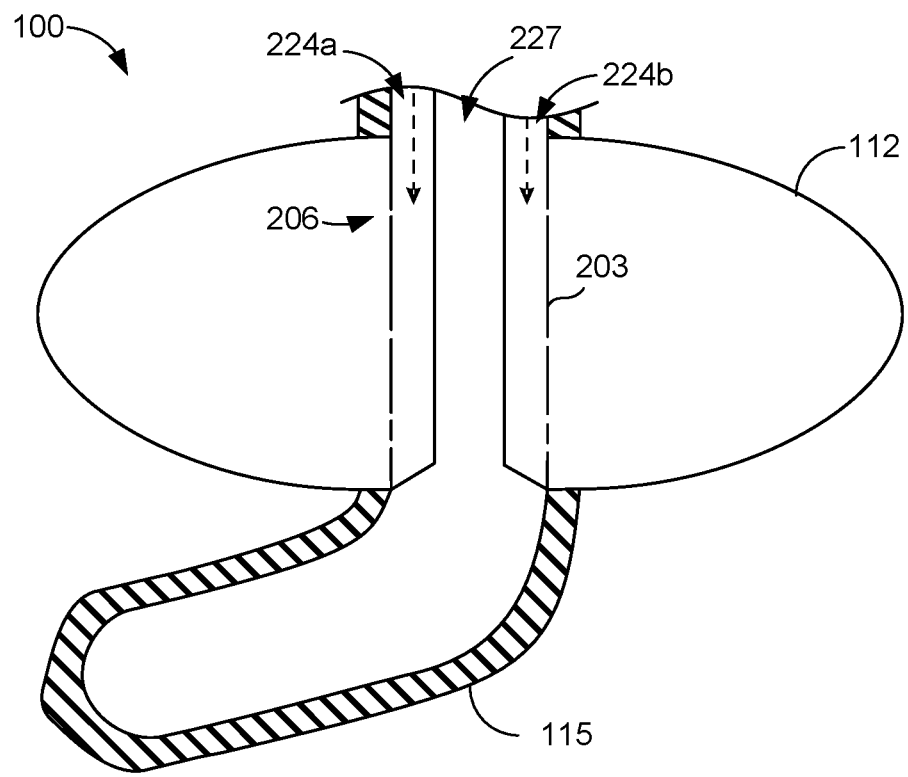
FIG. 2C is a third cross-sectional view of an inner tube of the balloon catheter from FIG. 1, according to one embodiment described herein.

With reference to FIG. 2C, shown is an enlarged cross-sectional view of the second end 121 of the balloon catheter 100 from FIG. 2A, in which an interior of the inner tube 203 of the catheter body 109 is exposed. In FIG. 2C, shown are the multiple openings 206 of the inner tube 203. Additionally, in this embodiment, the inner tube 203 is illustrated with a first balloon channel 224a and a second balloon channel 224b (collectively balloon channels 224). The balloon channels 224 are connected to the second port (FIG. 1) of the catheter hub 103 (FIG. 1), which is connected to the syringe 106. Thus, the gas or liquid from the syringe 106 (FIG. 1) can travel from the syringe 106 through the catheter hub 103 and into the one or more balloon channels 224. At the second end 121 of the catheter body 109, the gas or liquid travels from the balloon channels 224 through multiple openings 206 into the interior of the balloon 112, which causes the balloon 112 to inflate.

Further, the balloon catheter 100 comprises a guidewire channel 227 that enables a guide wire to travel from the third port of the catheter hub 103 through the catheter body 109 and through the inner tube 203. From the guidewire channel 227, the guide wire can pass through to the end 215 of the angled tip 115.

Figure 3:
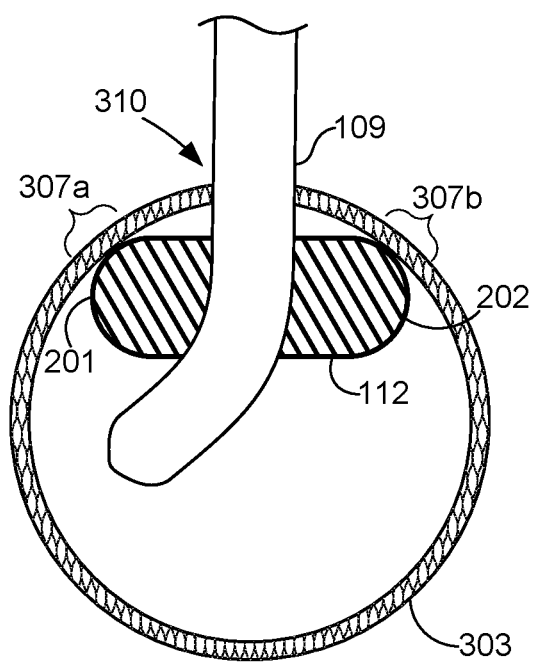
FIG. 3 is a view of the balloon catheter within a blood vessel in which the balloon is inflated, according to one embodiment described herein.

Next, with reference to FIG. 3, shown is the balloon catheter 100 within a lumen 303 (e.g., a blood vessel, a graft, etc.) in which the balloon 112 is inflated. As shown in the FIG. 3, the length "L" (FIG. 2A) of the balloon 112 is positioned perpendicular to a directional flow of the lumen 303. In other scenarios, the balloon 112 can be positioned parallel to a directional flow of the lumen 303 (FIG. 4A and FIG. 5A). In FIG. 3, the balloon 112 is positioned such that the first balloon end 201 and the second balloon end 202 of the balloon 112 are in contact with the interior surface of the lumen 303, as indicated in regions 307a,b. Since the distance "D2" (FIG. 2A) of the balloon catheter 100 is compact with respect to a diameter of the lumen 303, the angled tip 115 of the balloon catheter 100 can be rotated while the balloon 112 is inflated. Blood vessels, lumens, and other suitable blood transport carriers may have a diameter in a range between 5.75 mm and 6.25 mm. The top surface 209 (FIG. 2A) of the balloon 112 can be positioned adjacent or substantially near a top of the lumen 303 surrounding an access point 310 of the lumen 303, and then, the angled tip 115 can be rotated within the lumen 303.

Turning to FIG. 4A, shown is side view of the balloon catheter 100 within a blood vessel 401. In FIG. 4A, the top surface 209 of the balloon 112 can be positioned adjacent to the inner surface of the blood vessel surrounding a vascular access point 405. A sheath 404 is positioned at the vascular access point 405. The length "L" of the balloon 112 prevents the balloon 112 from passing through the vascular access point 405 while the balloon 112 is inflated. Typically, the vascular access point 405 has a diameter around 1.8 mm to 2.2 mm. The length "L" of the balloon 112 in an inflated state is sufficiently long enough to prevent the balloon 112 from being pulled out of the vascular access point 405 while the balloon 112 is inflated. Additionally, the compact dimensions of the balloon catheter 100 at the second end 121 provides enough spacing for the angled tip 115 to rotate from a first direction to a second direction within blood vessel 401. FIG. 4A also illustrates a guide wire 409 advanced from the angled tip 115.

Moving to FIG. 4B, shown is a side view of the balloon catheter 100 with a tapered balloon 412. The tapered balloon 412 comprises a top surface 415 that can have a sufficient surface area to prevent the tapered balloon 412 from passing through the vascular access point 405. The tapered balloon 412 also includes a bottom portion that has a smaller length than the top surface 415. Further, FIG. 4C illustrates a side view of the balloon catheter 100 with an alternative balloon 421.

Figure 5B:
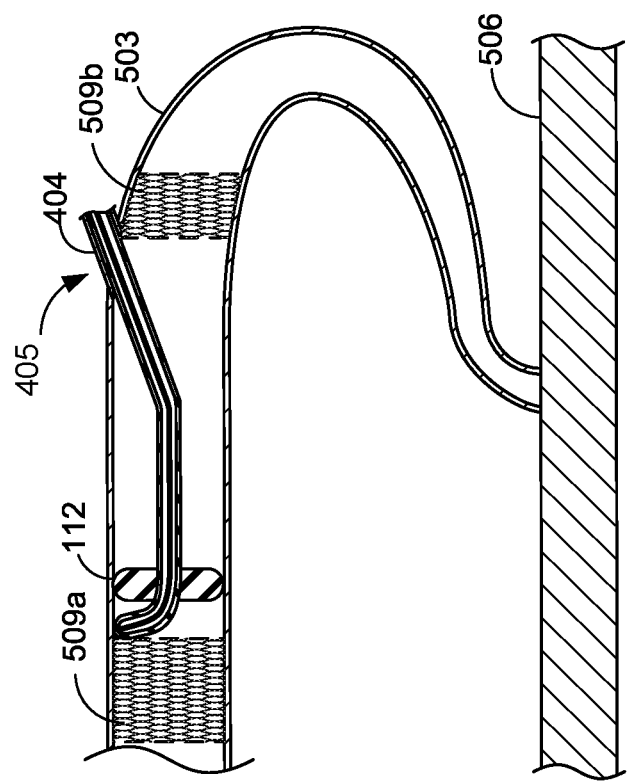
FIGS. 5A and 5B illustrate a side view of the balloon catheter inserted within a vein in an anterograde direction, according to one embodiment described herein.
Figure 5A:
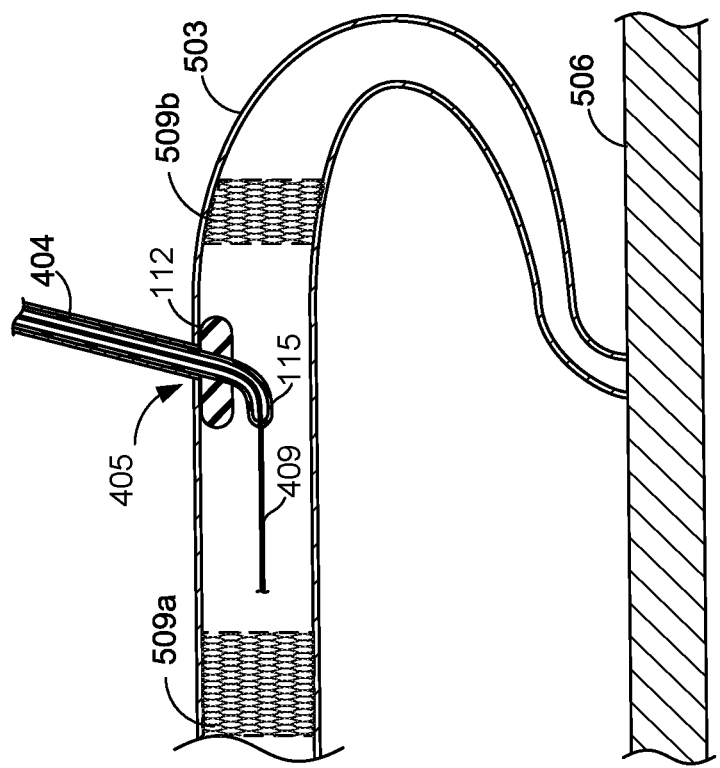
Figure 5C:
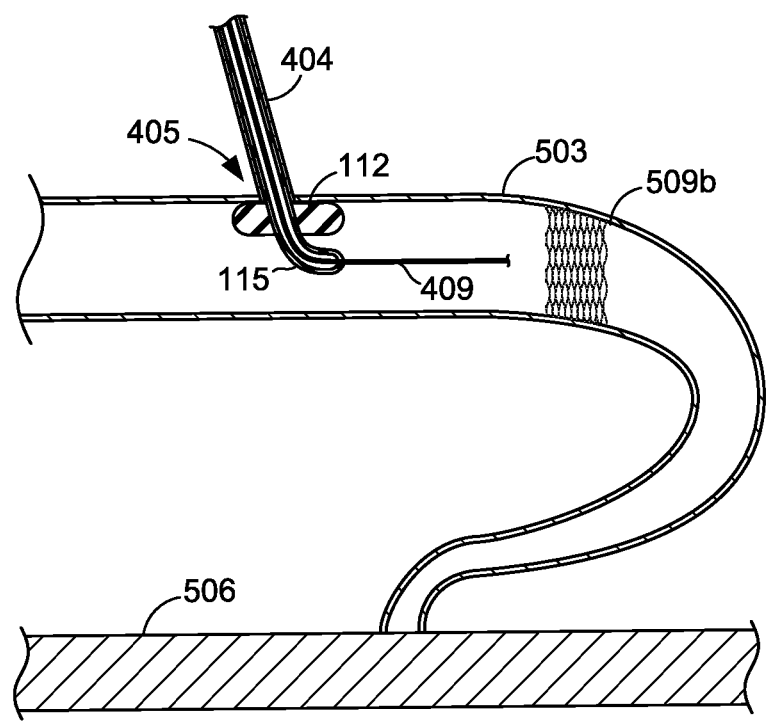
FIG. 5C illustrates a side view of the balloon catheter inserted within a vein in a retrograde direction toward an arterial end, according to one embodiment described herein.

FIGS. 5A through 5C illustrate side views of different stages of the balloon catheter 100 being used in at least a portion of a thrombectomy procedure. FIGS. 5A and 5B illustrate a side view of the balloon catheter 100 inserted within a vein 503 in an anterograde direction. FIGS. 5A and 5B illustrate the vein 503 connected to an artery 506. In FIG. 5A, the balloon 112 has been inflated at the vascular access point 405. FIG. 5A also illustrates that a guide wire 409 can be advanced in the anterograde direction in order to facilitate clearing blockage 509 a.

Additionally, FIG. 5B illustrates that the balloon 112 has been advance within the vein 503 in the anterograde direction. FIG. 5B also illustrates blockage 509a (e.g., clots) can be cleared by using the balloon 112. Particularly, the balloon 112 and the catheter body 109 have been manipulated such that the balloon 112 has been rotated about 90 degrees from its previous orientation in FIG. 5A. In this present configuration, the balloon 112 can be used to push blockage 509a further in the anterograde direction. Pushing the blockage 509a with balloon 112 can be effective in breaking down the blockage 509a in order to clear out the blood flow in the anterograde direction. After the anterograde direction (e.g., venous outflow) has been cleared, the balloon 112 can be pulled back to its position at the vascular access site 405, as illustrated in FIG. 5A.

At the vascular access point 405, the elongated shape of the balloon 112 has enough surface area on the top surface 209 (FIG. 2A) to provide vessel wall apposition, which prevents the balloon 112 from being pulled out the vein 503 at the vascular access point 405. Further, the guide wire 409 can be pulled back toward the catheter hub 103, such that the end of the guide wire is near the angled tip 115, within the angled tip 115, and within the catheter body 109. With the balloon 112 inflated, the balloon 112 and the angled tip 115 can be rotated within the vessel from the anterograde direction to a retrograde direction toward an arterial end. In some examples, the balloon 112 is rotated about 180 degrees about the vascular access point 405.

FIG. 5C illustrates a side view of the balloon catheter 100 oriented in the retrograde direction toward an arterial end after the balloon 112 has been rotated. FIG. 5C illustrates that blockage 509a has been cleared. At this point, in some scenarios, the guide wire 409 can be advanced. Then, the balloon 112 can be deflated, and the catheter body 109 is advanced over the guide wire 409. The sheath 404 can be advanced to further stabilize access. In this embodiment, once the catheter body 109 is advanced into the artery 506, the balloon 112 can be inflated again and used to complete a thrombectomy procedure by clearing the inflow of blockages 509b and any others.

Figure 6:
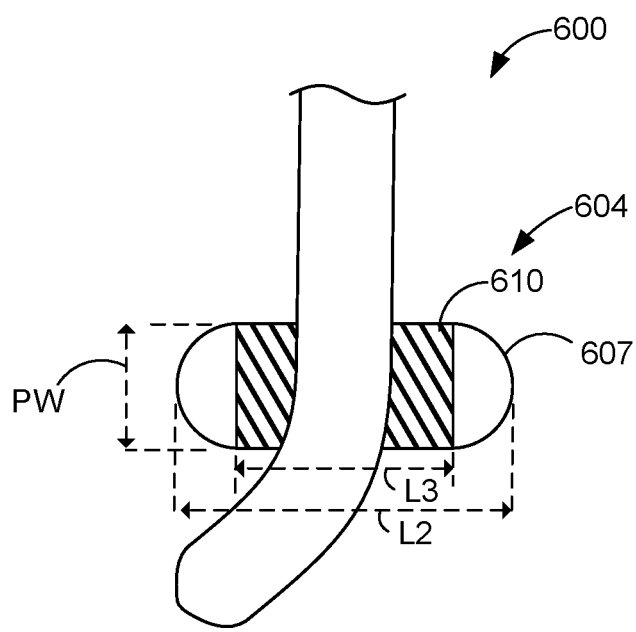
FIG. 6 illustrates an alternative balloon catheter with a two layer balloon, according to one embodiment described herein.

Next, FIG. 6 illustrates an alternative balloon catheter 600 with a two layer balloon 604. The two layer balloon 604 comprises an inner balloon layer 607 and an outer balloon layer 610. The outer balloon layer 610 can be attached to the inner balloon layer 607. In some examples, the inner balloon layer 607 and the outer balloon layer 610 may include a compliant balloon, a non-compliant balloon, and other suitable balloon materials.

In the non-limiting example of FIG. 6, the inner balloon 607 is a compliant balloon, and the outer layer 610 is comprised of non-compliant material. The inner balloon layer 607 can have varied shapes when inflated. The outer balloon layer 610 can be configured to restrict the shape of the inner balloon layer 607 as the inner balloon layer is inflated. In an inflated state, the outer balloon layer 610 can form a restrictive cylindrical shape that surrounds the inner balloon layer 607. The outer balloon layer 610 can permit the inner balloon layer 607 to expand to a predefined width "PW," and further expansion of the inner balloon layer 607 is limited to extend its length "L2". Accordingly, from a deflated state, the inner balloon layer 607 expands its width until it reaches a restrictive width "PW" of the outer balloon layer 610. Once the inner balloon layer 607 reaches the restrictive width "PW," the inner balloon layer 607 can further expand along its length "L2." In some embodiments, the outer balloon layer 610 can form a sleeve that surrounds the inner balloon 607. In an inflated state, the outer balloon layer 610 has a length "L3" that is smaller than the length "L2" of the inner balloon layer 607 in an inflated state.

Figure 7:
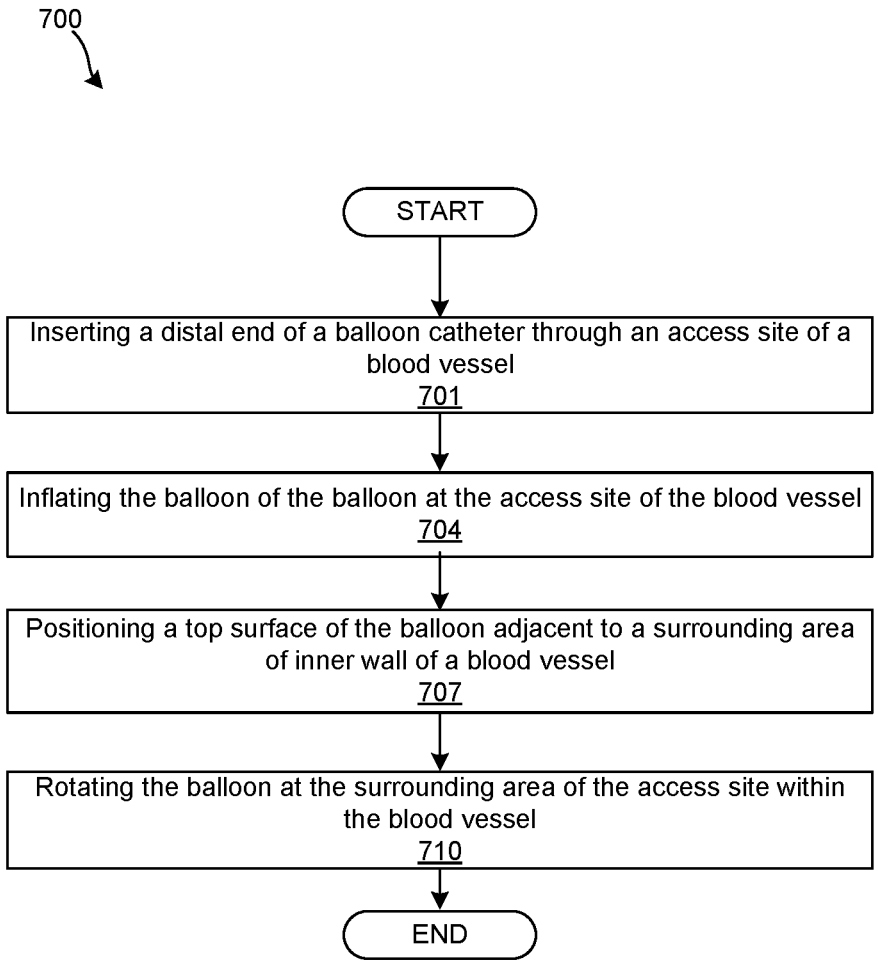
FIG. 7 is a flowchart illustrating a process for using the balloon catheter in FIG. 1, according to various embodiments of the present disclosure.

Referring next to FIG. 7, shown is a flowchart of a series of steps for using the various embodiments of the present disclosure. It is understood that the flowchart of FIG. 7 provides merely one example, among others, that may be employed to use the various embodiments of the present disclosure.

Beginning with box 701, a process 700 may include inserting a distal end of a balloon catheter through an access site 405 of a blood vessel. The distal end of the balloon catheter 100 may comprises an angled tip 115 and a balloon 112 adjacent to the angled tip 115. While the distal end is being inserted, the balloon 112 may be in a deflated state.

In box 704, the process 700 may include inflating, within the blood vessel, the balloon 112 of the balloon catheter 100 at an access site of a blood vessel. The balloon 112 can form an oblong shape in an inflated state, and the angled tip 115 is positioned in an anterograde direction of the blood vessel. In this orientation, the guidewire 409 and/or the balloon 112 can be used to clear blockages 509 in the anterograde direction. In some scenarios, the balloon 112 can be manipulated in different orientations within the blood vessel to push blockages 509.

In box 707, the process 700 may include positioning a top surface of the balloon 112 adjacent to a surrounding area of the access site within the blood vessel. While in an inflated state, the oblong shape of the balloon 112 can provide sufficient surface area to create enough vessel wall opposition in order to prevent the balloon 112 from being pulled out of the access site 405.

In box 710, the process 700 may include rotating the balloon 112, in an inflated state, at the surrounding area of the access site. As a result, the angled tip 115 can be repositioned from the anterograde direction to a retrograde direction toward an arterial end. In some examples, the angled tip 115 can be rotated about 180 degrees with respect to the access site 405. Then, the process 700 proceeds to the end.

Disjunctive language such as the phrase "at least one of X, Y, or Z," unless specifically stated otherwise, is otherwise understood with the context as used in general to present that an item, term, etc., may be either X, Y, or Z, or any combination thereof (e.g., X, Y, and/or Z). Thus, such disjunctive language is not generally intended to, and should not, imply that certain embodiments require at least one of X, at least one of Y, or at least one of Z to each be present.

It should be emphasized that the above-described embodiments of the present disclosure are merely possible examples of implementations set forth for a clear understanding of the principles of the disclosure. Many variations and modifications may be made to the above-described embodiment(s) without departing substantially from the spirit and principles of the disclosure. All such modifications and variations are intended to be included herein within the scope of this disclosure and protected by the following claims.

Therefore, the following is claimed:

1. A balloon catheter, comprising:
a catheter body having an elongated cylindrical shape and comprising a first end, a second end, and a longitudinal axis aligned between the first and second ends;
a balloon comprising a top surface coupled to the second end, a bottom surface spaced distally from the top surface, wherein the balloon is inflatable to an oblong shape having a length perpendicular to the longitudinal axis that is greater than its width along the longitudinal axis; and
an angled tip fixed to and extending from the bottom surface along a tip axis that extends from the bottom surface at an angle relative to the longitudinal axis, wherein, when inflated, a distance from the top surface of the balloon to an end of the angled tip is in a range of 0.5 mm to 6 mm.

2. The balloon catheter of claim 1, wherein the oblong shape comprises a donut-shape or an oval shape.

3. The balloon catheter of claim 1, wherein, when inflated, the width of the balloon is in a range of 0.5 mm to 6 mm.

4. The balloon catheter of claim 1, wherein the balloon comprises at least one of a compliant balloon or a non-compliant balloon.

5. The balloon catheter of claim 1, wherein the angle of the angled tip comprises an angle in a range of 135 degrees to 165 degrees with respect to the longitudinal axis of the catheter body.

6. The balloon catheter of claim 1, wherein when the balloon is inflated, the angled tip can be changed from a first direction to a second direction while in a lumen.

7. The balloon catheter of claim 1, wherein the balloon comprises an inner balloon layer and an outer balloon layer that attaches to the inner balloon layer, wherein the outer balloon layer restricts the width of the balloon during an inflated state.

8. The balloon catheter of claim 7, wherein the length comprises a first length, and when inflated, the outer balloon layer has a second length that is less than the first length of inner balloon layer.

9. The balloon catheter of claim 7, wherein the inner balloon layer comprises a compliant balloon and the outer balloon layer comprises a non-compliant balloon material.

10. The balloon catheter of claim 1, wherein the balloon comprises two outer regions along the width and a central region along the width, wherein the two outer regions have a first balloon material composition and the central region has a second balloon material composition.

11. The balloon catheter of claim 1, wherein the balloon comprises a tapered region from the top surface to a bottom region of the balloon.

12. The balloon catheter of claim 1, wherein a distance from the bottom surface of the balloon to an end of the angled tip is in a range from 1.75 mm to 3.25 mm.

13. The balloon catheter of claim 1, wherein a curved surface of the angled tip begins adjacent to the bottom surface of the balloon.

14. The balloon catheter of claim 1, wherein when inflated the length of the balloon is in a range between 0.5 mm-6.25 mm.

15. A balloon catheter, comprising:
a catheter body comprising a first end, a second end, and a longitudinal axis aligned between the first and second ends;
a balloon comprising a top surface coupled to the second end and a bottom surface spaced distally from the second end, wherein the balloon is inflatable to an oblong shape having a length perpendicular to the longitudinal axis that is greater than its width along the longitudinal axis; and
an angled tip fixed to and extending from the bottom surface along a tip axis that extends at an obtuse angle relative to the longitudinal axis, the angled tip comprising a curved region beginning immediately at the bottom surface and a substantially straight portion extending from the curved region parallel to the tip axis, wherein a distance from the top surface to an end of the angled tip parallel to the longitudinal axis is less than 6.5 mm.

16. The balloon catheter of claim 15, wherein the substantially straight portion of the angled tip terminates at a rounded end.

17. The balloon catheter of claim 15, wherein, when the balloon is in an inflated state the balloon defines first and second side ends defining the length of the balloon, an end of the angled tip does not extend laterally past the first side end in the inflated state.

18. A balloon catheter, comprising:
- a catheter body comprising a first end, a second end, and a longitudinal axis aligned between the first and second ends;
- a balloon comprising a top surface coupled to the second end and a bottom surface spaced distally from the second end, wherein the balloon is inflatable to an oblong shape having a length perpendicular to the longitudinal axis that is greater than its width along the longitudinal axis; and
- an angled tip integrally formed with the balloon and extending from the bottom surface along a tip axis that extends at an obtuse angle relative to the longitudinal axis, the angled tip comprising a curved region beginning immediately at the bottom surface, a substantially straight portion extending from the curved region parallel to the tip axis, and terminating in a rounded end, wherein a distance from the top surface to the rounded end parallel to the longitudinal axis is less than 6.5 mm.

* * * * *